United States Patent [19]
Slater et al.

[11] Patent Number: 5,482,054
[45] Date of Patent: Jan. 9, 1996

[54] EDOSCOPIC BIOPSY FORCEPS DEVICES WITH SELECTIVE BIPOLAR CAUTERY

[75] Inventors: Charles R. Slater, Fort Lauderdale; Matthew A. Palmer, Miami; John R. Whittier, Miami; Aaron R. Zwiefel, Miami, all of Fla.

[73] Assignee: Symbiosis Corporation, Miami, Fla.

[21] Appl. No.: 265,217

[22] Filed: Jun. 24, 1994

Related U.S. Application Data

[63] Continuation of Ser. No. 16,595, Feb. 11, 1993, abandoned, which is a continuation-in-part of Ser. No. 959,247, Oct. 9, 1992, Pat. No. 5,312,400, Ser. No. 865,913, Apr. 9, 1992, Pat. No. 5,228,451, and Ser. No. 837,046, Feb. 18, 1992, which is a continuation of Ser. No. 521,766, May 10, 1990, Pat. No. 5,133,727.

[51] Int. Cl.⁶ ................................................. A61B 10/00
[52] U.S. Cl. ........................................... 128/751; 606/46
[58] Field of Search ..................................... 128/749, 751; 606/41, 46–52, 205–208

[56] References Cited

U.S. PATENT DOCUMENTS

| 4,953,559 | 9/1990 | Salerno | 128/751 |
| 5,217,458 | 6/1993 | Parins | 606/48 |

FOREIGN PATENT DOCUMENTS

| 0518230A1 | 12/1992 | European Pat. Off. | A61B 17/39 |
| 0518230 | 12/1992 | European Pat. Off. | 606/46 |

*Primary Examiner*—Angela D. Sykes
*Assistant Examiner*—Samuel Gilbert
*Attorney, Agent, or Firm*—David P. Gordon

[57] ABSTRACT

An endoscopic bipolar cautery biopsy forceps device has a conduit, a pair of articulable opposed jaws, two conductive pull wires, and an actuator. The articulable opposed jaws are located at the distal end of the conduit. Each jaw is provided with a cutting surface at its distal end and a tang at its proximal end. At least a portion of the cutting surface is electrically conductive and a portion of the tang is electrically conductive and electrically coupled to the conductive cutting surface. The remainder of the jaw is preferably non-conductive or is coated with an insulator. The conductive pull wire is coupled to the conductive portion of the tang of each jaw and is insulated as it extends through the conduit to a handle portion which includes the actuator. The actuator is coupled to the proximal ends of the pull wires so that movement of the actuator pulls the pull wires and articulates the jaws. The actuator is also provided with an electrical coupling device which electrically couples to the proximal ends of the pull wires and permits easy connection to an electrical cautery source.

30 Claims, 11 Drawing Sheets

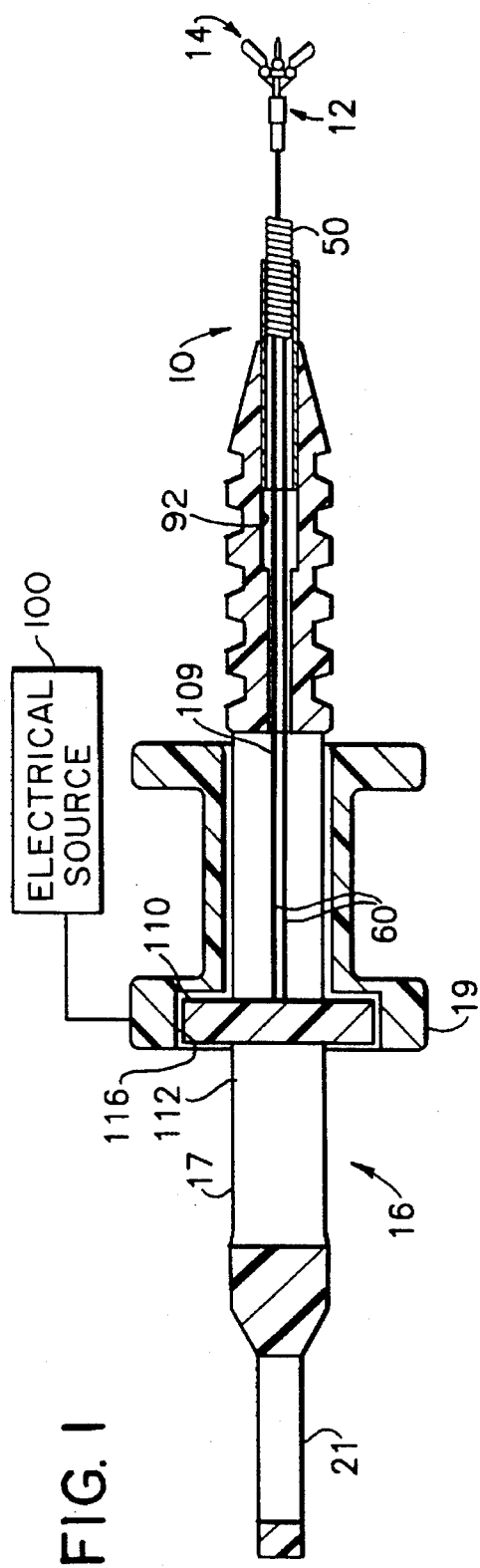
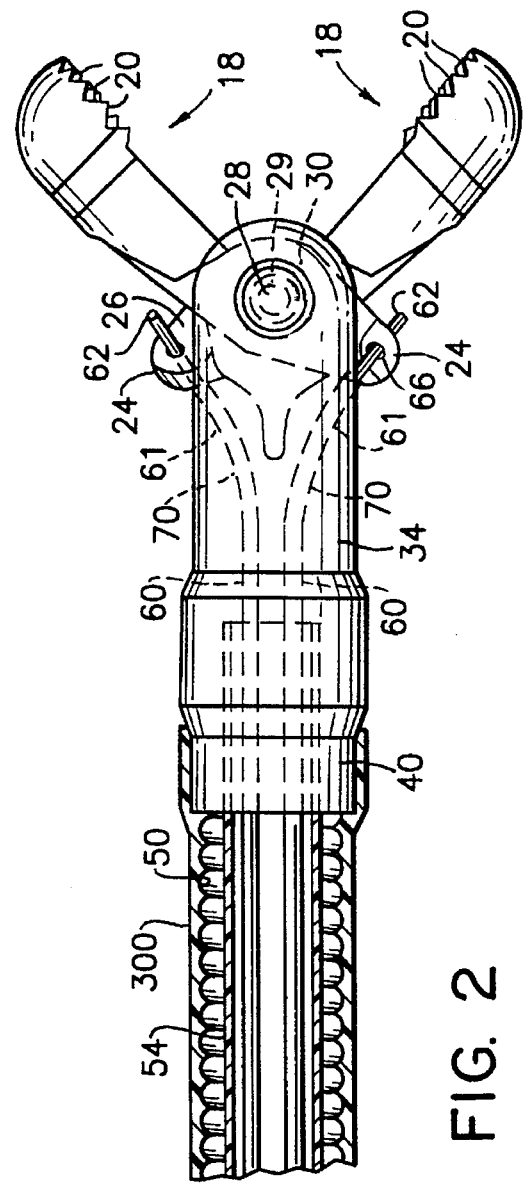
FIG. 1
FIG. 2

EDOSCOPIC BIOPSY FORCEPS DEVICES WITH SELECTIVE BIPOLAR CAUTERY

This is a continuation of application, Ser. No. 08/016, 595, filed Feb. 11, 1993 now abandoned, which in turn is a continuation-in-part of coassigned Ser. No. 07/837,046 filed Feb. 18, 1992 (which is a continuation of Ser. Nos. 07/521, 766 filed May 10, 1990 now issued as U.S. Pat. No. 5,133,727), 07/865,913 filed Apr. 9, 1992 now U.S. Pat. No. 5,228,451, and 07/959,247 filed Oct. 9, 1992 now U.S. Pat. No. 5,312,400 all of which are hereby incorporated by reference herein in their entireties.

BACKGROUND OF THE INVENTION

The present invention relates to endoscopic biopsy forceps medical devices. More particularly, the invention relates to endoscopic biopsy forceps devices having bipolar cautery capabilities.

A number of different types of endoscopic biopsy forceps devices are in common use. Ordinarily, these devices are of complicated construction, requiring the manufacturing and machining of precise miniature components, which are therefore generally quite expensive. They most often include opposing jaws for grasping and tearing tissue for biopsy. One early example of an endoscopic biopsy forceps instrument is shown in U.S. Pat. No. 3,895,636 (1975) to Schmidt, where a pair of cup shaped jaws having an annular rim which mate with a hub and a sharpened trocar is disclosed. The Schmidt device, however, does not disclose the ability to conduct cautery operations. While numerous improvements have recently been made to endoscopic biopsy forceps instruments, such as disclosed in U.S. Pat. Nos. 4,763,668 to Macek et al., 4,721,116 to Schintgen et al., 4,815,476 to Clossick, 4,817,630 to Schintgen et al., 4,880,015 to Nierman, and 4,887,612 to Esser et al., none of these patents disclose an instrument having cautery ability.

Clearly, where traumatic procedures such as taking a biopsy are being conducted, the ability to conduct endoscopic cautery procedures is desirable in order to stem bleeding. While both monopolar and bipolar endoscopic cautery instruments are known (such as disclosed in U.S. Pat. No. 4,418,692 to Guay), increasingly, bipolar cautery is preferred because it is less traumatic to the patient. In bipolar cautery instruments, the electric current path is from one electrode, through the tissue to be cauterized, and then through to the other electrode and out the instrument. Thus, only that tissue between the two electrodes is being cauterized. On the other hand, in monopolar instruments, the patient effectively becomes the second electrode, and the current must be dissipated through the patient. Thus, control of the cautery location is not exact, and tissue surrounding the tissue to be cauterized is also subject to different degrees of cautery.

In U.S. Pat. No. 4,763,660 to Jaeger, a bipolar endoscopic microelectrocautery device is shown. The Jaeger device also discloses a device for obtaining biopsies. However, the device disclosed in Jaeger requires a number of different single function "instrument heads" only one of which may be attached at any time to the instrument for performing a specific function such as grasping, cutting, or cauterizing. Thus, the biopsy forceps "head", is incapable of cauterizing, while the cauterizing "head" is incapable of obtaining a biopsy. This arrangement still does not permit the surgeon to cauterize at the biopsy site at the time of taking a biopsy.

SUMMARY OF THE INVENTION

It is therefore an object of the invention to provide a endoscopic biopsy forceps having a pair of jaws which function as bipolar electrodes.

It is also an object of the invention to provide an endoscopic biopsy forceps where only a selected portion of the surface of the biopsy jaws is conductive.

It is another object of the invention to provide a bipolar cautery capable endoscopic biopsy forceps where the jaws of the biopsy forceps are operable by a pair of pull wires contained within a coil shaft where the pull wires also function to provide electrical connection to the jaws.

It is a further object of the invention to provide methods for manufacturing cautery capable biopsy forcep jaws and assembling them on a clevis so that only portions of the jaws are electrically conductive.

It is yet another object of the invention to provide mechanisms on a bipolar cautery capable endoscopic biopsy forceps which easily permit the connection of the endoscopic device to an electrical source.

In accord with these objects which will be discussed in detail below, the bipolar cautery biopsy forceps of the present invention generally includes: a conduit; a pair of jaws pivotally mounted at the distal end of the conduit and having electrically conductive distal portions and electrically conductive proximal portions, wherein the jaws are electrically insulated from each other when the jaws are in a relative open position; a pair of electrically conductive pull wires which are insulated as they extend through the conduit but which electrically and mechanically contact the jaws at their electrically conductive proximal portions; and an actuation means coupled to the pull wires for opening and closing the jaws. Typically, the proximal ends of the conductive pull wires are uninsulated and terminate in a contact or coupling means which couples to an electrical cautery source. The electrical cautery source may be foot activated or hand activated, and/or the bipolar cautery biopsy forceps may include an electrical switch for actuating the cautery function.

The jaws of the bipolar cautery biopsy forceps are preferably constructed with a proximal conductive uninsulated tang into which the distal end of the pull wire connects, a distal conductive cutting surface, and a pivot point between the proximal tang and distal cutting surface around which the jaws pivot for opening and closing. In an open position, the jaws are insulated from each other. A clevis which is insulated from the jaws is preferably mounted on the distal end of the conduit and provides an insulated pivot pin around which the jaws pivot. The cutting surfaces of the distal ends of the jaws preferably include metal cutting teeth. Some or all of the teeth may be insulated, but at least a portion of at least one tooth on each jaw is uninsulated so as to provide bipolar electrodes.

Several different jaw embodiments are provided. According to one embodiment, the jaws are formed via investment casting or MIM (metal injection molding) and then coated with an insulating polymer or ceramic material. Alternatively, the jaws are formed by insert molding metal teeth and tang components which may be formed via casting, stamping, or photochemical milling or machining (PCM) in a non-conductive polymer material. A third jaw embodiment involves modling the jaws from ceramic (CIM) and selectively plating the teeth and tang areas with a suitable metal (e.g. gold).

Preferred aspects of the invention include: providing an insulating combination sleeve-washer for insulating the jaws and clevis pin from each other or alternatively providing an integral insulating clevis pin—washer for insulating the jaws; forming the conduit as a flexible coil; mounting the jaws on a clevis coupled to the distal end of the flexible coil;

forming the proximal end of each jaw as a tang and coupling the pull wires to the tangs by means of Z-bends in the wires; and securing a handle to the proximal end of the main coil wherein the handle comprises a central slotted shaft about which a displaceable spool is disposed. In the preferred embodiment, proximal movement of the spool with respect to the central shaft effects a pull on the pull wires so as to create a pivotable motion of the tangs on the proximal end of the jaws, thereby causing the jaws to close. Movement of the spool distally with respect to the central shaft effects a compression on the pull wire thus causing movement of the tangs thereby causing the jaws to open.

Other preferred aspects of the invention include: fitting a cross block or blocks and mating the cross block(s) within a slot across the proximal end of the spool; coupling the proximal ends of the pullwires to the cross block(s); and providing a coupling in the spool for an electrical cautery source.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation view, partially in cross-section of a bipolar cautery biopsy forceps assembly of the invention;

FIG. 2 is an enlarged side elevation view of the distal end of the selective bipolar cautery biopsy forceps instrument of FIG. 1;

FIG. 8b is a side elevation view of the conductive insert of FIG. 8a;

DETAILED DESCRIPTION OF THE PREFERRED EMBODIMENTS

Figure 3A:
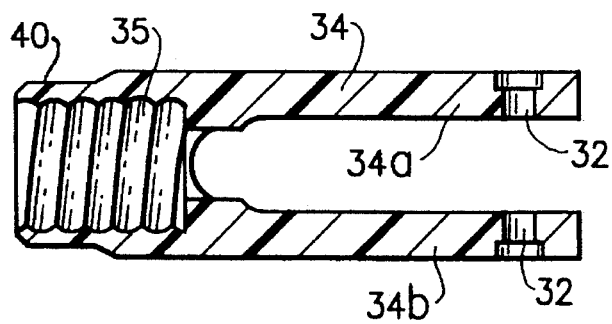
FIG. 3a is an enlarged top plan view of the clevis of FIG. 2.
Figure 3B:
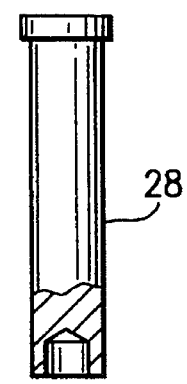
FIG. 3b is an enlarged top plan view of the clevis pin of FIG. 2.

Referring now to the drawings in detail and particularly to FIGS. 1 and 2, there is shown a biopsy forceps assembly 10, having a distal end 12, comprising a jaw assembly 14, and a proximal end 16 comprising a handle 17, a spool 19 and a thumb ring 21 for manipulation of the assembly. The handle 17 is provided with a longitudinal slot 112 in communication with an axial bore 92. A cross block 110 (or other pull-wire holding means) is slidable within slot 112 and is carried by a diametrical slot 116 in the proximal end of spool 19. The cross block 110 is coupled to pull wires 60 as described in more detail below with reference to FIGS. 5, and 5a–5h. The pull wires extend through axial bore 92 into a main coil 50 and both the main coil 50 and the pull wires 60 extend to the distal end 12 of the biopsy forceps 10.

Figure 6:
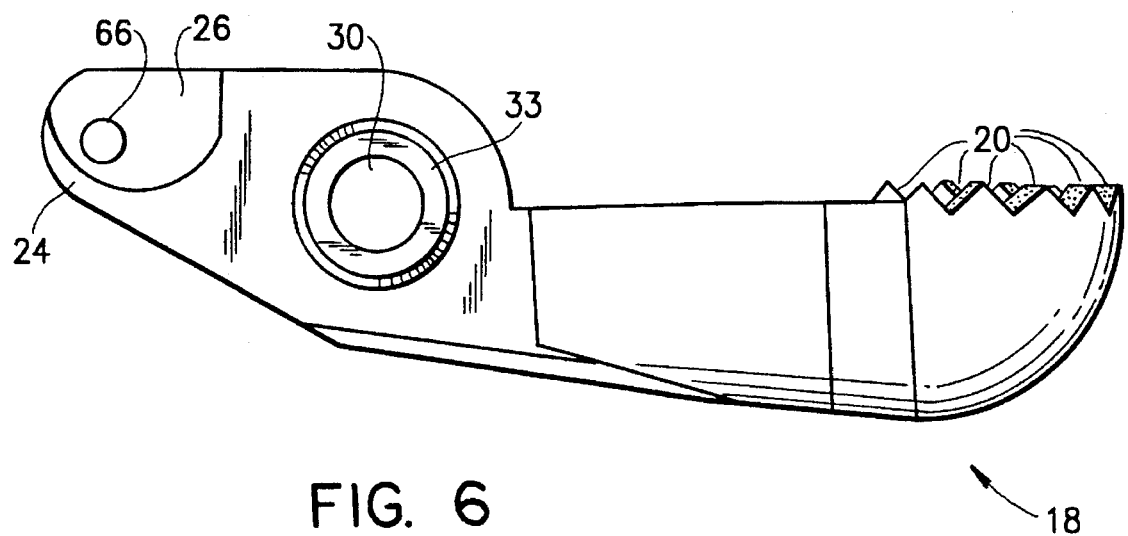
FIG. 6 is side elevation view of a conductive jaw with selective polymer coating.

The jaw assembly 14 comprises e pair of jaws 18, each of which is preferably a duplicate of the other. Each jaw 18, as may be seen in FIGS. 2, 3c, 3e, and 6, is a generally elongated somewhat hemispherically shaped structure having a distal end and a proximal end. On the distal end of each jaw 18 is an array of teeth 20 generally radially directed about a point "R", as exemplified in FIG. 3c. Each jaw 18 has a generally longitudinal center line as may be seen in FIGS. 3c and 3e. The teeth 20 on one side of the longitudinal center line of each jaw 18 are displaced by one half pitch from the corresponding teeth 20 on the other side of the longitudinal center line. The displacement by one half pitch of the teeth on one side of the jaw 18 relative to those corresponding teeth 20 on the other longitudinal side of the jaw 18 permits the same casting to be used for both the upper and lower jaws of the jaw assembly 14. The radial arrangement of the teeth 20 as best seen in FIGS. 3c and 6 allow jaws 18 when they close onto one another to automatically mate and effectuate proper alignment of their teeth 20.

Figure 3C:
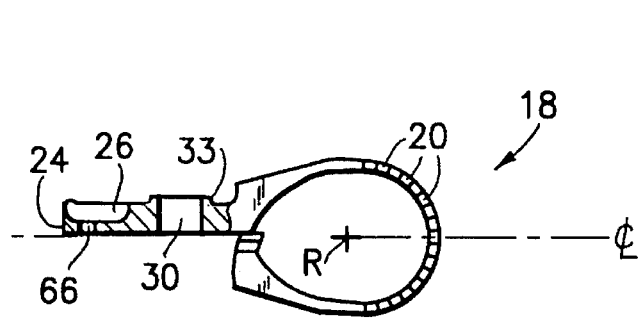
FIG. 3c is an enlarged top plan view of the lower jaw of FIG. 2.
Figure 3D:
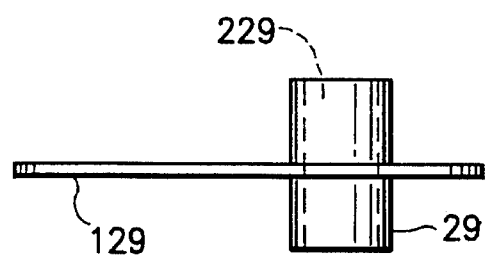
FIG. 3d is an enlarged top plan view of an insulating sleeve and washer of FIG. 2.
Figure 3E:
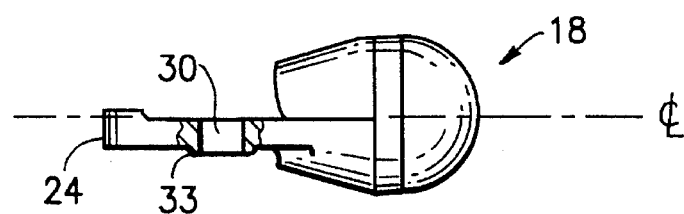
FIG. 3e is an enlarged top plan view of the upper jaw of FIG. 2.

Turning now to FIGS. 2 and 3a–3e, the proximal end of each jaw 18 comprises a tang 24 which has a generally semicircular recess position 26 on its outer side. A bore 30 extends transversely through the midsection of the jaw 18 between the distal and proximal ends of each jaw 18, and a clevis pin 28 extends through the bore 30 on each respective jaw 18. Each jaw 18 has an annular boss 33 disposed about the outer face of its bore 30, as shown in FIGS. 3c and 3e. The boss 33 acts as a bearing surface to reduce the typical friction found on prior art endoscopic biopsy forceps devices. The clevis pin 28 (FIG. 3b) is received in a hole 32 in clevis 34 as shown in FIG. 3a. The clevis 34 extends proximally, as shown in FIG. 2, into a hub 40 and is provided with an inner threaded portion 35 for receiving a main tubular coil 50. As described in more detail below, the selectively conductive jaws 18 are insulated from each other and from the clevis pin 28, which is normally stainless steel, by a one piece non-conductive combination washer/sleeve 29 (seen in FIG. 3d) which is preferably a polymer with a thickness of approximately 0.005–0.015 inches. The washer/sleeve 29 has a washer portion 129 and a sleeve portion 229. The washer portion 129 prevents the facing surfaces of the proximal and pivot portions of the jaws 18 from contacting each other, while the sleeve portion 229 prevents a conductive clevis pin from electrically coupling the jaws 18. It will be appreciated that the clevis 34 is preferably non-conductive. A preferred material for forming the clevis is a VECTRA polymer available from Hoechst-Celanese, or an equivalent. The clevis pin 28 (FIG. 3b) may be made of polymer; in which case the washer/sleeve 29 need only include the washer portion 129.

Figure 4:
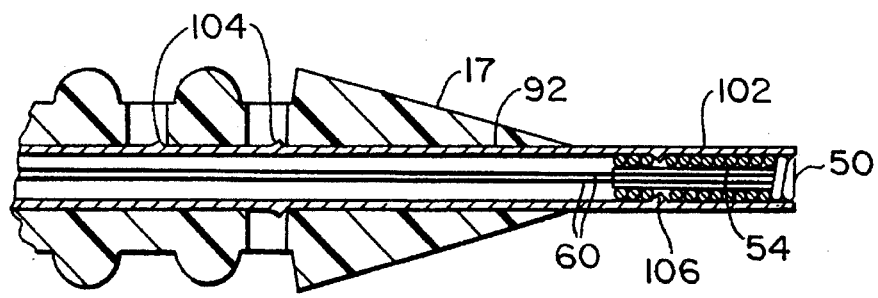
FIG. 4 is a cross sectional view of the coil connection to the handle of the bipolar cautery biopsy forceps instrument of FIG. 1.

In the preferred embodiment of the invention, the main coil 50 is a comprised of a stainless steel rod of approximately 0.021 inch diameter which is tightly wound and preloaded into a main coil having an outer diameter of approximately 0.09 inches and a length of approximately seven feet. As seen in FIG. 2, at least a portion of the coil 50 as well as a portion of the clevis hub 40 are covered by a stiffening mechanism 300. Although the coil is made stiffer than would be otherwise, damage to an endoscope through which the biopsy forceps device is inserted is avoided, as the shrink wrap is lubricious and smooth. A polyethylene (PE) sheath 54 also extends through approximately the entire length inside coil 50 as shown in FIGS. 1 and 4. Pull wires 60 extend through sheath 54 and sheath 54 acts as a bearing between pull wires 60 and the lumen of the main coil 50.

The distal end of each pull wire 60 has an uninsulated Z-bend therein. The Z-bend of each pull wire 60 has a portion 62 which is rotatably disposed in the recess 26 in the tang 24 of each cutter jaw 18 by extending through a bore 66 near the proximal end of the tang 24, as best shown in FIGS. 2 and 3c. Each pull wire 60 has a reflex curve 70 as shown in FIG. 2 extending between their distal ends and the distal end of the main coil 50. The reflex curve 70 helps to open the cutter jaws 18 when the spool 19 on the handle 17 is displaced distally thereto. The remainder of each pull wire is covered with an insulating sheath 61 up to its proximal end which is described in more detail below.

Referring now to FIGS. 1 and 4, a crimp ferrule 102 is shown extending from inside the axial bore 92 of the handle outwardly, so that the crimp ferrule 102 extends slightly distally of the distal end of the handle 17. The crimp ferrule 102 is secured to the inner walls of the bore 92 by barbs 104. The crimp ferrule is disposed about the main coil 50, and the coil 50 is secured within the crimp ferrule 102 by one or more crimps 106. A strain relief sheath (not shown) surrounds the distal end of the handle and the proximal end of the coil, and limits twist and movement of the main coil 50 with respect to the bore 92 while preventing a sharp bend of the coil 50 at the distal end of the handle 17.

Figure 5:
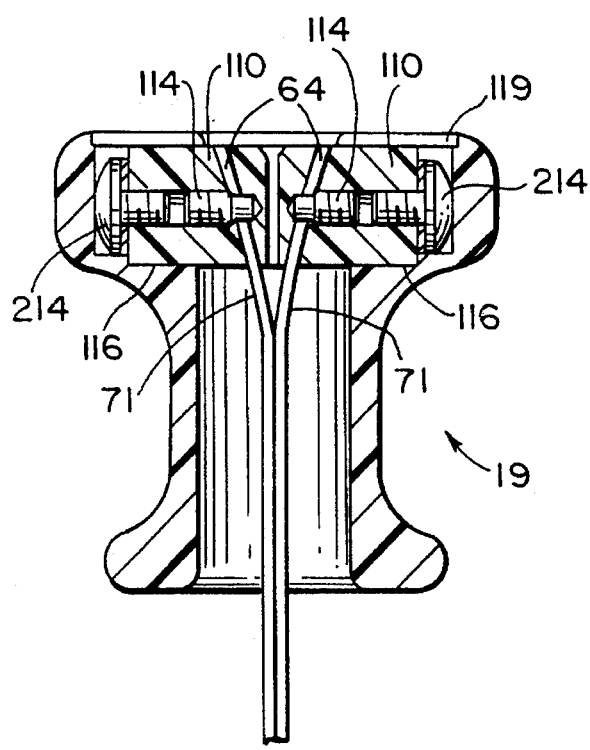
FIG. 5 is a cross sectional view of the spool of FIG. 1 which utilizes a first embodiment of T-shaped pull-wire holding blocks according to the invention.
Figure 5J:
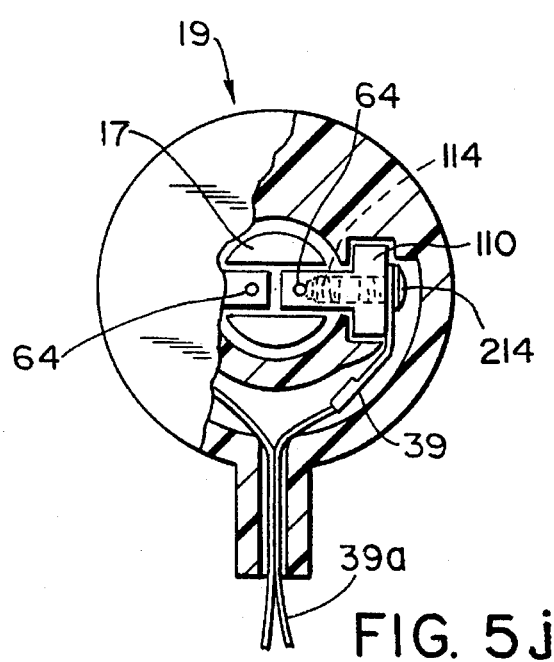
FIG. 5j is a top view in partial cross section of the spool of FIG. 5.

Turning now to FIGS. 1, 5, and 5-1 the proximal end of the pull wires 60 extend through the proximal end of the main coil 50 and through metal anti-kinking tubes 109 (see FIG. 5j), and are locked into non-conductive T-shaped blocks 110 carried by spool 19 in slot 116, as shown in FIG. 5. In this embodiment, the anti-kinking tubes 109 of pull wires 60 are bent at 71 into a "Y" configuration as shown, and a proximal electrical connection 64 of the pull wires is made by set screws 114 and button screws 214. Set screws 114 secure the proximal electrical connection 64 of pull wires 60 to the T-shaped blocks 110, while the button screws 214 are used to secure conductor connectors 39 which connect to wires 39a from an electrical source 100 (FIG. 1) to the set screws 114. Typically, as shown in FIG. 5j, the conductor connector 39 is placed between the button screw 214 and the T-block 110, and the button screw is tightened so that an electrical connection is made between the conductor and the T-shaped block. The nonconductive T-shaped blocks 110 pass through slot 112 in the handle 17 which is in communication with the axial bore 92 (FIG. 1) and are held in place. The proximal ends 64 of the pull wires 60 are uninsulated and pass through the T-shaped blocks 110. The pull wires 60 are secured in the T-shaped blocks 110 by set screws 114. Movement of the spool 19 which is disposed about the central shaft of handle 17 thereby effects movement of the pull wires 60 disposed within the main coil 50, the distal ends of which are attached to the tangs 24 on the cutter jaws 18 as shown in FIGS. 1 and 2.

As mentioned above, the pull wires are electrically conductive and insulated along their length except for their distal Z-bend connection 62 to the tangs 24 of the jaws 18 and their proximal connection at 64 to an electrical source. Thus, pull wires 60 are separated at the T-shaped blocks 110 and secured by separate set screws 114 as shown in FIG. 5 whereby they are electrically coupled to contacts (described in detail below) for coupling with an electrical source 100. A recess 119 in spool 19 is provided for an insulated cover (not shown). The electrical source 100 may be foot or hand activated, and if desired an electrical switch (not shown) may be provided on the spool in order to provide additional control.

Figure 5A:
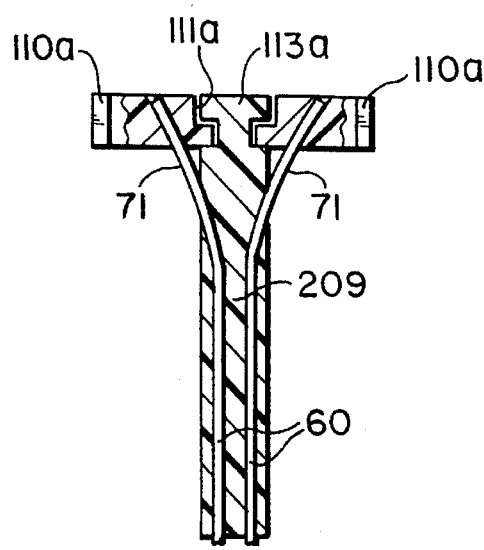
FIG. 5a is a cross sectional view of a second embodiment of T-shaped pull-wire holding blocks.
Figure 5B:
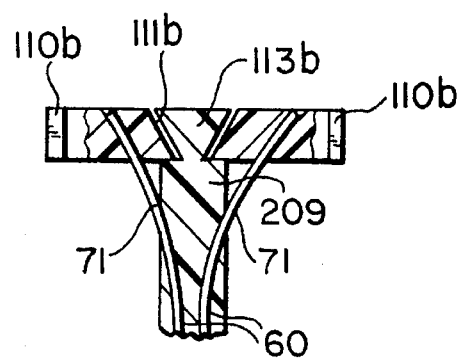
FIG. 5b is a view similar to FIG. 5a but of a third embodiment of T-shaped pull-wire holding blocks.

Alternative configurations of the T-shaped blocks 110 are shown in FIGS. 5a and 5b. In particular, and as seen in FIGS. 5a and 5b, the pull wires 60 are bent at 71 and insert molded into an ABS or other plastic sheath 209 described below with reference to FIG. 5h. The sheath 209 is provided with a flare 113a or 113b which engages a space 111a or 111b between a pair of T-shaped blocks 110a or 110b. As seen respectively in FIGS. 5a and 5b, the flare may be stepped (113a) or ramped (113b). Electrical connection is made by means of set screws as shown in FIG. 5.

Figure 5C:
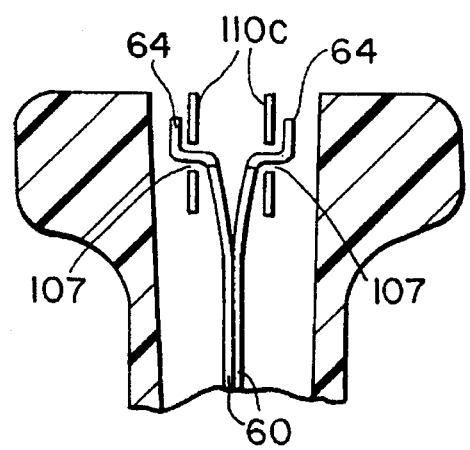
FIG. 5c is a cross sectional view of pull-wire holding plates.
Figure 5D:
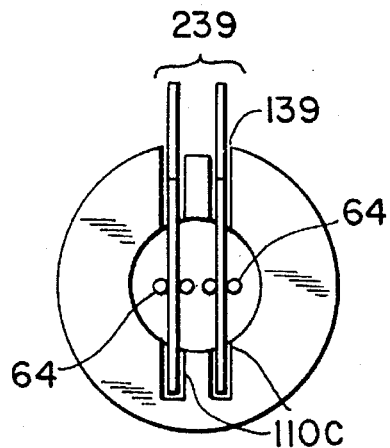
FIG. 5d is a top plan view of the holding plate embodiment of FIG. 5c showing cautery plug connections.
Figure 5E:
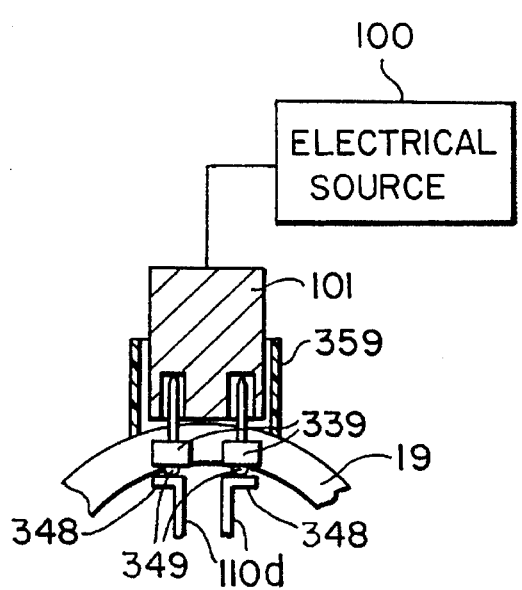
FIG. 5e is a view similar to FIG. 5d of an alternate embodiment of cautery plug connections.

Yet another embodiment of a pull-wire holding or engaging mechanism is shown in FIGS. 5c and 5d. Here the pull-wire engaging mechanism 110c comprises a pair of substantially parallel conductive plates spaced apart from each other. The plates are provided with holes 107 for receiving the uninsulated proximal ends 64 of the pull wires 60. In this embodiment, the uninsulated ends 64 of pull wires 60 are provided with Z-bends similar to those at their distal ends. The Z-bends at 64 engage holes 107 in plates 110c as shown in FIG. 5c. As shown in FIG. 5d, the substantially parallel conductive plates 110c are supported by recesses in the spool, and terminate at the side of spool 19 with an electrical socket 139 for receiving blades 239 of a male cautery plug. Alternatively, the plates could terminate in male prongs for connecting to a female cautery plug. For example, as shown in FIG. 5e, prongs 339 are mounted in the spool 19. The electrical connection between the prongs 339 and the metal plates 110*d* is provided by biasing the bent ends 348 of metal plates 110*d* against ball contacts 349 integral with prongs 339. A collar 359 integral with spool 19 surrounds prongs 339 to aid in securing the female cautery plug 101 coupled with an electrical source 100 to the spool 19.

Figure 5F:
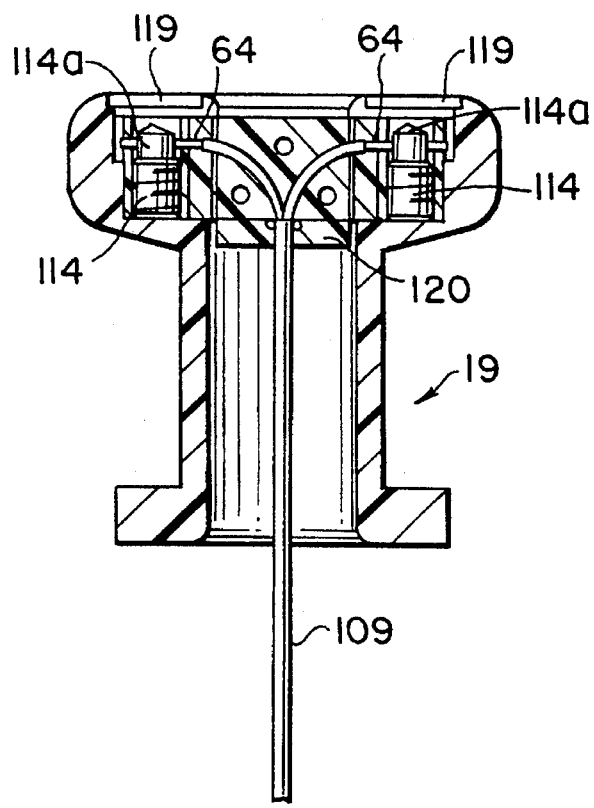
FIG. 5f is a view similar to FIG. 5 but with a cross block in place of the T-blocks.

In lieu of the T-shaped block or metal plate embodiments of FIGS. 5, and 5*a*–5*e*, a non-conductive cross block 120 shown in FIG. 5*f* is used for gripping pull wires 60. The non-conductive cross block 120 passes through slot 112 in the handle 17 which is in communication with the axial bore 92 (FIG. 1). The proximal ends 64 of the pull wires 60 are uninsulated and pass through the cross block 120. The pull wires 60 are secured in the cross block 120 by set screws 114. Electrical connection is made by set screws 114 screwed into metal anchor blocks 114*a* located within spool 19 at either end of cross block 120. A recess 119 in spool 19 is provided for an insulated cover (not shown).

Figure 5G:
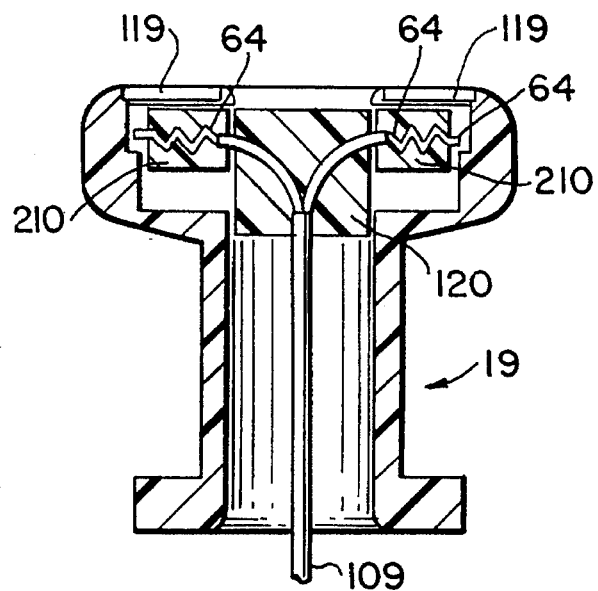
FIG. 5g is a view similar to FIG. 5f but with an alternate pull wire gripping fixture.
Figure 5H:
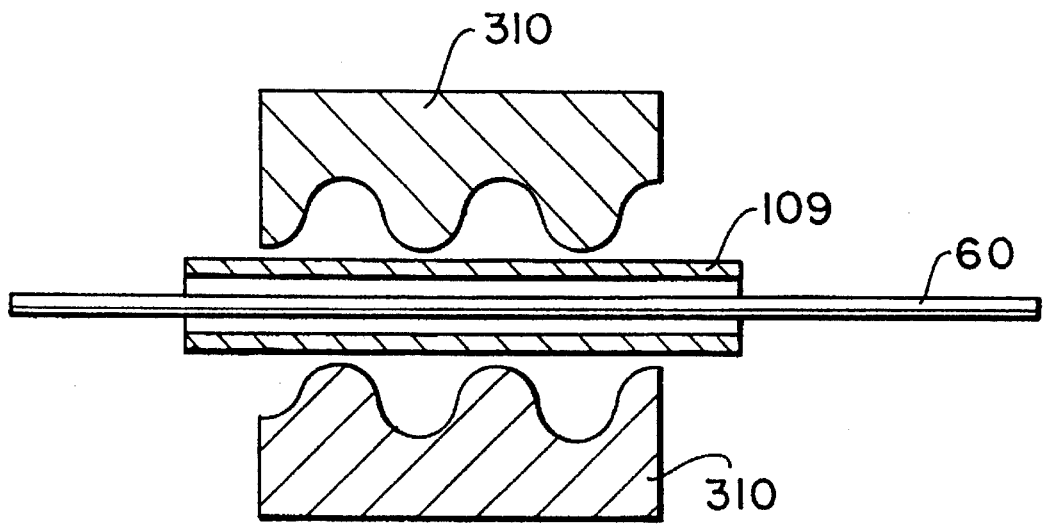
FIG. 5h is a cross sectional view of a die for crimping the pull wires and covering sheath used in FIG. 5g.

In lieu of set screws 114 with anchor blocks, 114*a*, fixtures 210 shown in FIG. 5*g* are used for securing and electrically coupling the pull wires 60. In this embodiment, the pull wires 60 and anti-kinking tubes 109 are crimped by die 310 as shown in FIG. 5*h*. The crimped tubes 109 with pull wires 60 are then fitted into a corresponding recess 210 in the spool 19.

It will be appreciated that regardless of the particular pull-wire holding mechanism used, some means must be provided for receiving a cautery wire. Thus, the wire may be soldered or otherwise connected to the bipolar cautery forceps instrument, or a plug or receptacle may be provided on the end of the wire for an oppositely corresponding plug or receptacle on the instrument.

Figure 5I:
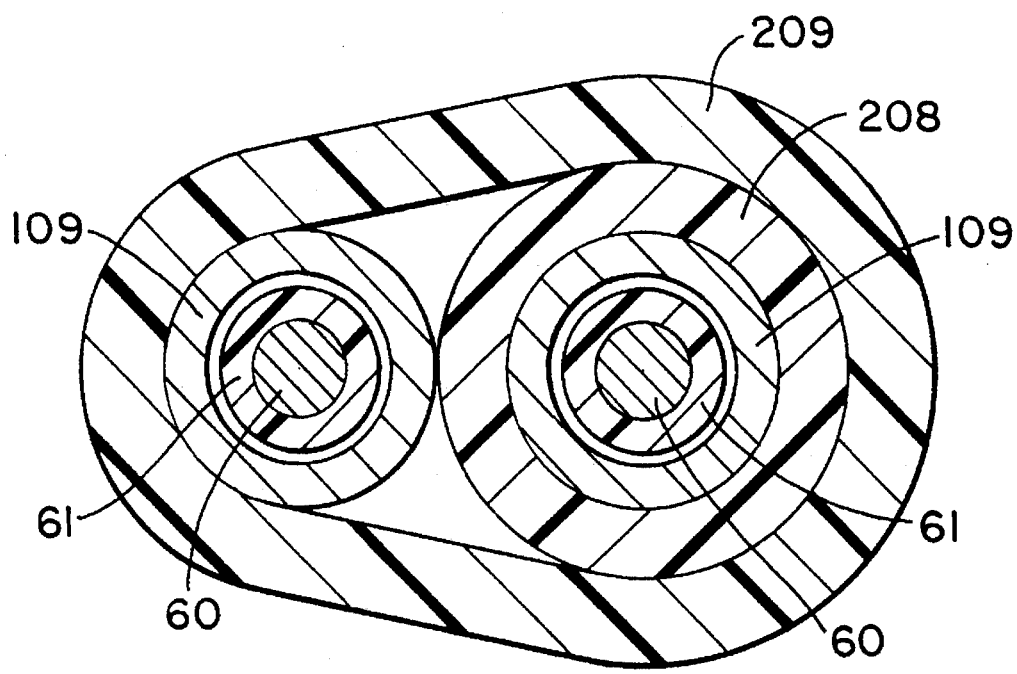
FIG. 5i is a cross sectional view of one embodiment of covering sheath for the pull wires.

FIG. 5*i* shows an arrangement of inner and outer sheaths which protect and insulate pull wires 60. As mentioned above, metal anti-kinking tubes 109 are preferably utilized around the insulation 61 of pull wires 62 to prevent the pull wires 60 from kinking. In order to prevent the metal anti-kinking tubes 109 from touching, an insulative sheath 208 is preferably placed around the anti-kinking tube 109 of one of the pull wires 60. Both the inner sheath 208 and the other anti-kinking tube 109 of the other pull wire 60 are then preferably covered by an outer sheath 209 which holds the tubes 109 in close proximity for easy passage through the instrument.

While the arrangements discussed above with reference to FIGS. 1–5*h* above provide a bipolar cautery biopsy forceps device which may be used both for taking biopsies and conducting cautery operations, it will be appreciated that the entire surfaces of the jaws 18 constitute the electrodes. In many applications, however, such large electrodes are not desirable as it is desirable to control the specific points of cautery.

Turning now to FIG. 6, a jaw 18 which has a limited or selective conducting (electrode) surface is seen. The jaw 18 is preferably formed by casting a conductive metal as described in parent application Ser. No. 07/837,046 hereto, and subsequently coating the jaw with a very thin highly insulating polymer such as PARYLENE manufactured by Union Carbide. The PARYLENE preferably is deposited evenly on the jaw surfaces by applying it in a tumbling or other process in a vacuum at room temperature. Because the proximal portion of the jaw 18 must make contact with the uninsulated distal portion of the pull wire 60, and because at least a portion of the distal portion of the jaw must be uninsulated so that it can act as an electrode, the teeth 20 and connecting portion 66 of tang 24 are preferably masked before coating so that those surfaces remain conductive. Alternatively, if the teeth and tang are not masked, after the polymer coating has been applied it is removed from the teeth 20 and connecting portion 66 of tang 24 via machining, grit blasting, or other processing. It will be appreciated that instead of removing the polymer from the connecting portion 66, the hole 66 can be drilled after coating to provide an uninsulated surface. It will also be appreciated that in this embodiment of the jaw, the insulating washer/sleeve 29 is not absolutely required because the clevis hole will be coated with insulation. However, use of the insulating washer/sleeve is still preferred in order to prevent current from passing through the insulation of closely abutting portions of the jaws. Moreover, as coating may eventually wear off the inside diameter of hole 30, use of sleeve 29 is advisable.

Figure 7:
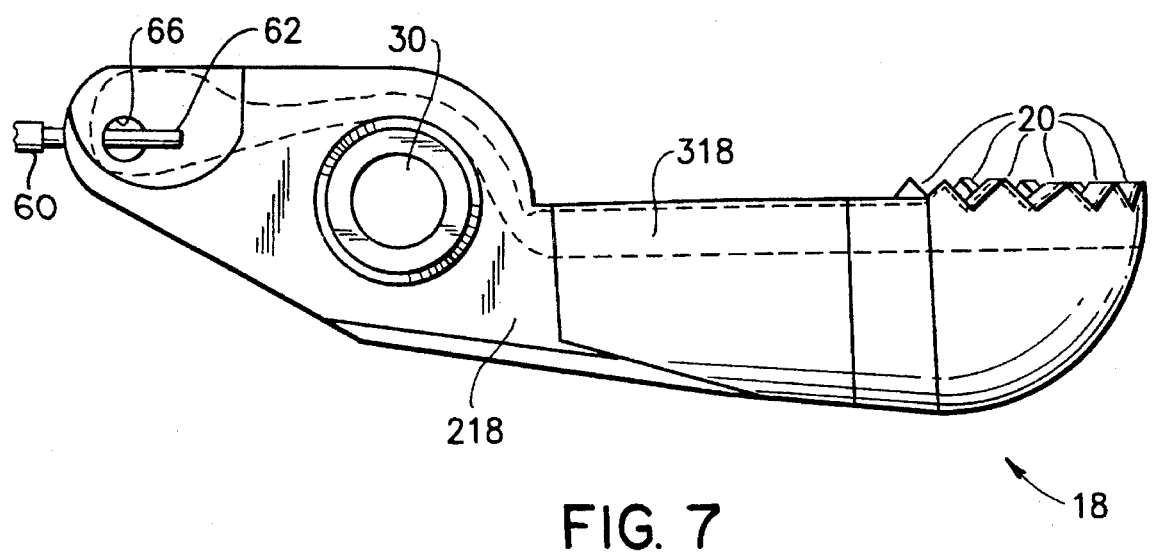
FIG. 7 is a side elevation view of an injection molded plastic jaw whose teeth are rendered conductive by an external conductive trace.

Another mechanism for creating a selectively conductive jaw is shown in FIG. 7. Here the jaw 18 is formed via injection molding a ceramic 218 such as alumina, zirconia, etc. Thereafter, the formed jaw is provided with conductive plating traces 318 which are provided on the ceramic surface or in the ceramic, as well as on the teeth 20 and at the pull wire connection 66. In this manner, the teeth 20 are electrically connected to the pull wire connection 66. The plating may be applied by sputtering or by other suitable procedures.

Figure 8A:
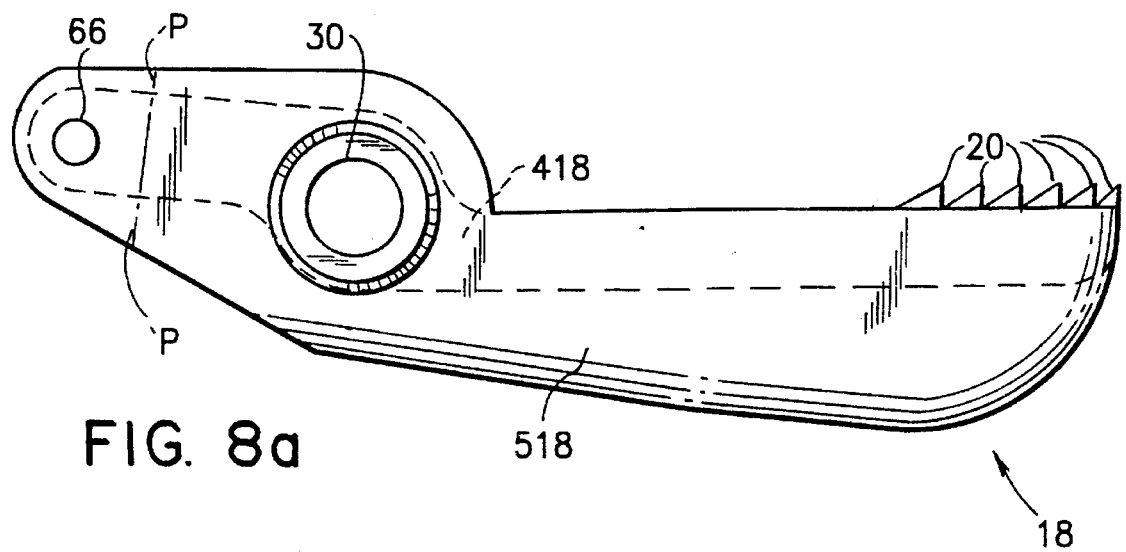
FIG. 8a is a side elevation view of selectively conductive insert injection molded jaw.
Figure 8B:
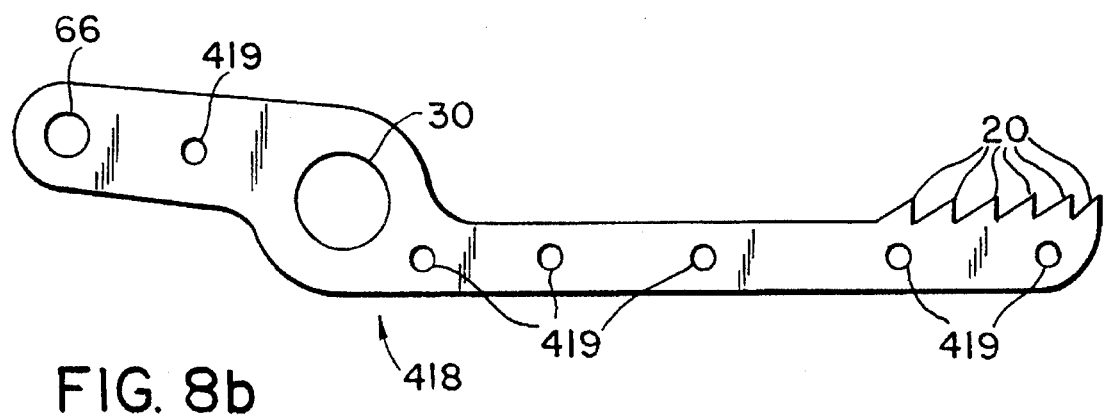
Figure 8C:
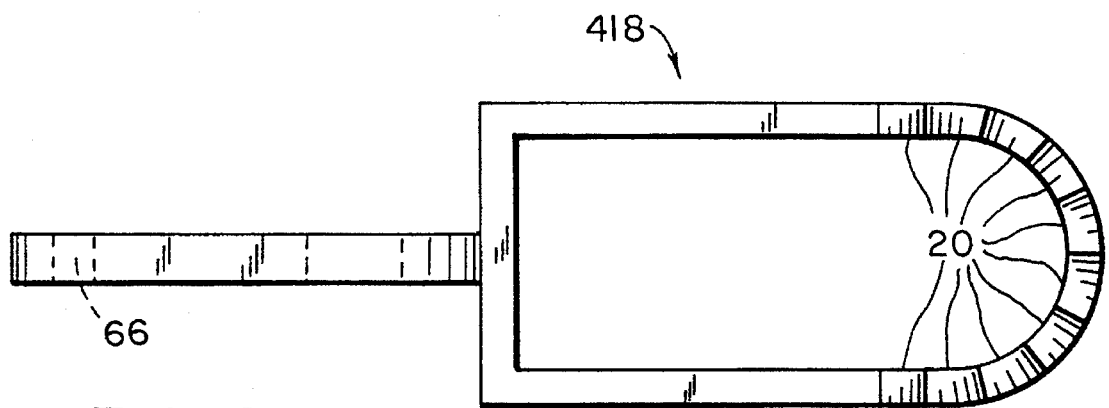
FIG. 8c is an enlarged top plan view of the conductive insert of FIG. 8b.

Yet another mechanism for constructing a selectively conductive jaw is shown in FIGS. 8*a*–8*c*. Here a conductive skeleton portion 418 of the jaw is formed by casting, stamping, or by photochemical milling or machining, and the skeleton portion 418 is preferably provided with staking holes 419. The skeleton is then used as an insert for in an insert-type injection mold which is filled with plastic 518. While in the mold, the plastic flows through the staking holes 419 and anchors the conductive skeleton 418 mechanically. The mold is designed such that at least the conductive teeth 20 are exposed while the remainder of the skeleton 418 is encased within plastic 518. As seen in phantom in FIG. 8*a* (at P-P), if desired, the pull wire connection area 66 of the skeleton 418 may also be exposed during insert molding so that it is not necessary to drill out hole 66 in order to guarantee electrical connection to the pull wire. Also, because of the manner in which the jaws are formed, it will be appreciated that the plastic 518 may be caused to totally cover some of the teeth, or a portion of some or all of the teeth.

FIGS. 9, 9*a*, 9*b*, and 9*c* show an alternate embodiment of jaws 918 according to another aspect of the invention. These jaws are similar to the jaws 18 shown in FIGS. 2, 3*c* and 3*e*, as each jaw has a clevis pin bore 930 with an annular boss 933, a tang 924 and a recess 926 for receiving a pull wire (not shown) through a pull wire bore 966. Unlike the jaws 18 described above, however, jaws 918 are provided with teeth 920 which extend around the entire perimeter of the jaw. As shown best in FIG. 9*a*, teeth 920 are arranged in a distal array 921, a proximal array 922 and two side arrays 923. The proximal and distal arrays are radially directed about points e1 and e2 respectively which lie on center line CL somewhat proximal of and somewhat distal of a center point R. The straight side arrays 923 are arranged to join the proximal and distal curved arrays. The teeth 920 are, like the teeth 20 of jaws 18, displaced by one half pitch relative to the center line.

Figure 9:
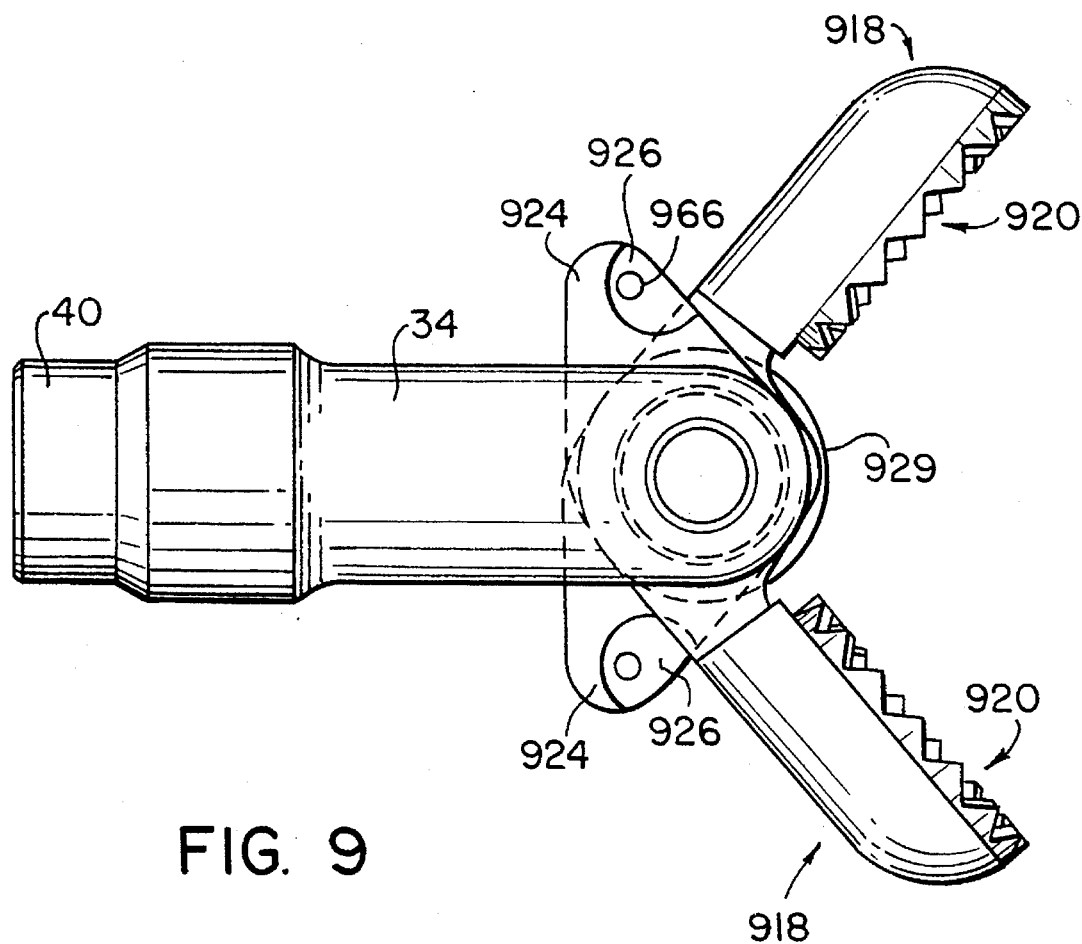
FIG. 9 is a view similar to FIG. 2 showing an alternate embodiment of jaws.
Figure 9A:
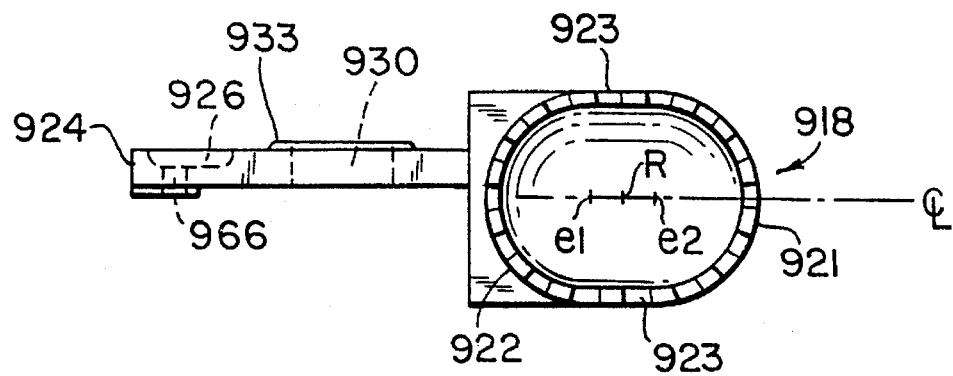
FIG. 9a is an enlarged plan view of one of the jaws of FIG. 9.
Figure 9B:
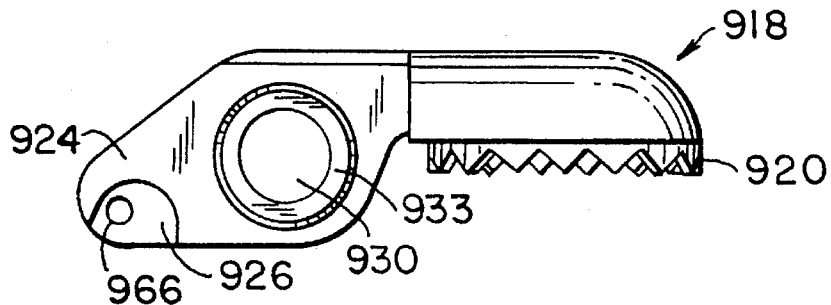
FIG. 9b is a side elevation view of one of the jaws of FIG. 9.
Figure 9C:
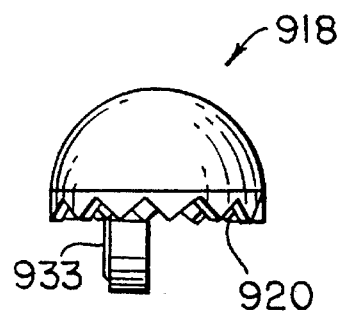
FIG. 9c is a front view of the jaw of FIG. 9b.
Figure 9D:
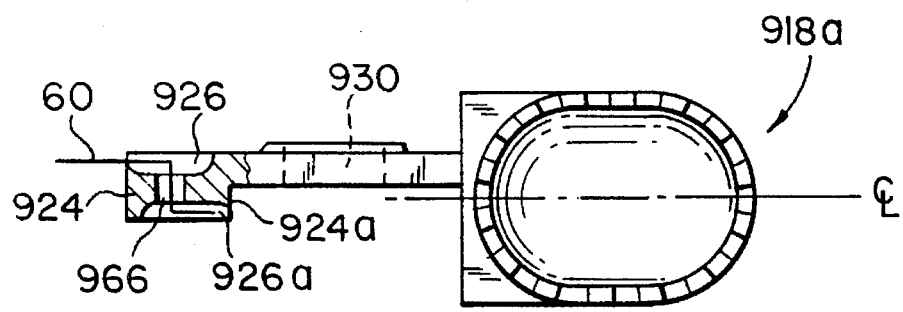
FIG. 9d is a view similar to FIG. 9a but of a second alternate embodiment of jaws.

FIG. 9d shows another alternate embodiment of jaw 918a. This jaw is similar to jaw 918 described above except for its tang 924. In this embodiment, the tang 924 includes a lateral extension 924a which crosses center line CL. The lateral extension 924a is provided with an interior recess 926a which communicates with recess 926 through pull wire bore 966. It will also be noticed that recess 926a is slightly offset from recess 926. This offset better accommodates the Z-bend in pull wires 60. It should be noted however, that with the arrangement of FIG. 9d, the jaws of the biopsy forceps instrument cannot be identical. Additional details of a similar tang arrangement may be obtained with reference to copending Ser. No. 07/680,392 which is hereby incorporated by reference herein.

Figure 10:
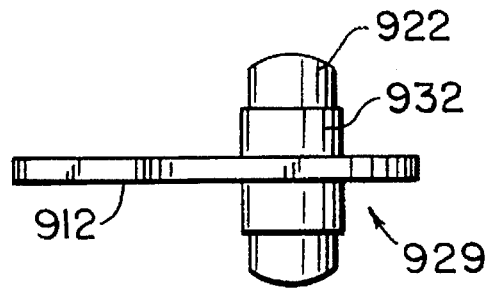
FIG. 10 is a view similar to FIG. 3d showing an alternate embodiment of washer, sleeve and clevis pin.
Figure 10A:
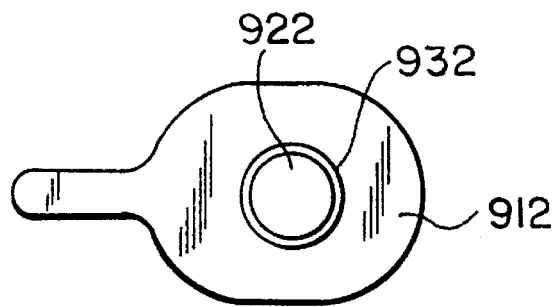
FIG. 10a is a top view of FIG. 10.
Figure 10B:
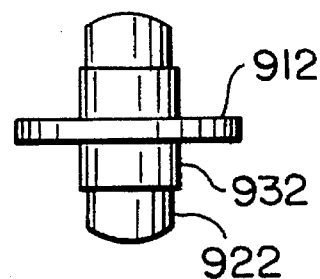
FIG. 10b is an end view of FIG. 10.

FIGS. 10, 10a, and 10b show an alternate embodiment of the insulating washer/sleeve and clevis pin discussed above with reference to FIGS. 3b and 3d. In the embodiment of FIGS. 10, 10a and 10b, the washer, sleeve, and clevis pin are a single non-conductive unit 929. The non-conductive unit 929 has a generally flat washer portion 912 which lies between jaws 18 (alternatively 918), a generally cylindrical (solid) sleeve portion 932, which resides in bores 30 (alternatively 930), and a generally cylindrical (solid) clevis pin portion 922 which engages hole 32 of clevis 34 (FIG. 3a). Forming the sleeve, washer and clevis pin as a single unit 929 has the advantage of preventing fluids and other biological material from entering the space between the jaws. It also lends to a more reliable construction since the clevis pin is unable to disengage from the clevis. To assemble the jaws and clevis using this embodiment, the non-conductive clevis 34 (FIG. 3a) must be flexible enough so that its arms 34a, 34b can be spread while the jaws with the non-conductive clevis pin/washer/sleeve unit 929 are inserted between them. The clevis 34 should be resilient enough so that after the jaws and the washer/sleeve/clevis pin 929 are aligned between arms 34a, 34b, the arms will grip the clevis pin of the unit in the holes 32 of the clevis arms. It should also be appreciated that while it is not absolutely necessary for the non-conductive unit 929 to have the stepped sleeve portion 932, such a step is desirable to provide a bearing or stop surface for the clevis.

There have been described and illustrated herein several embodiments of a bipolar cautery biopsy forceps. While particular embodiments of the invention have been described, it is not intended that the invention be limited thereto, as it is intended that the invention be as broad in scope as the art will allow and that the specification be read likewise. Thus, while particular configurations of the handle and spool have been disclosed, it will be appreciated that other configurations could be utilized without sacrificing the selective bipolar cautery features of the invention. In fact, various aspects of the described embodiments could be mixed and matched in combination in order to obtain desired results. Other handle arrangements could be used so long as the pull wires are moved relative to the coil and so long as an electrical connection for the pull wires is provided. Also, while particular configurations have been disclosed in reference to the selectively conductive surface of the jaws, it will be appreciated that other configurations could be used as well. Further, while several embodiments of electrical connection to an electrical source have been shown, it will be apparent to those skilled in the art that other types of electrical connections could be adapted for use with the invention. In addition, while the main coil has been shown as such, it will be appreciated that this main conduit need not be a coil but could be any other type of flexible or rigid conduit which meets the requirements of the invention. It will therefore be appreciated by those skilled in the art that yet other modifications could be made to the provided invention without deviating from its spirit and scope as so claimed.

We claim:

1. An endoscopic bipolar cauterizing biopsy forceps for use with an electrical cautery supply, comprising:

a) a conduit having proximal and distal ends;

b) a pair of opposed jaws hingedly disposed at said distal end of said conduit, said jaws each having a proximal end portion with an electrically conductive portion and a distal end portion with an electrically conductive portion, wherein the electrically conductive portions of the proximal and distal end portions of each particular law are electrically coupled to each other, and said electrically conductive portions of said opposed jaws are insulated from each other when said opposed jaws are in an open position, said jaws each forming a cup for receiving a biopsy sample;

c) a pair of flexible electrically conductive pull wires, each having a proximal and a distal end, said pull wires extending through said conduit and insulated from each other in said conduit, the distal end of each of said pull wires being mechanically and electrically coupled to the proximal end portion of a respective one of said opposed jaws, and the proximal ends of said pull wires being capable of being coupled to the electrical cautery supply; and d) actuation means disposed at the proximal end of said conduit and coupled to said pull wires for moving said pull wires to open and close said jaws relative to each other.

2. An endoscopic bipolar cauterizing biopsy forceps according to claim 1, further comprising:

e) electrical source coupling means electrically coupled to said proximal ends of said pull wires for coupling the electrical cautery supply to said pull wires.

3. An endoscopic bipolar cauterizing biopsy forceps according to claim 1, wherein:

said jaws each have an electrically non-conductive outer surface except for a cutting surface on said distal end portion and except for said electrically conductive portion of said proximal end portion.

4. An endoscopic bipolar cauterizing biopsy forceps according to claim 1, wherein:

each of said jaws comprises a conductive skeleton insert molded in a non-conductive body.

5. An endoscopic bipolar cauterizing biopsy forceps according to claim 1, wherein:

each of said jaws comprises a non-conductive body with an electrically conductive tooth on said distal end portion of said jaws and an electrically conductive tang on said proximal portion of said jaws, wherein said electrically conductive tooth and said electrically conductive tang are electrically connected.

6. An endoscopic bipolar cauterizing biopsy forceps according to claim 1, further comprising:

e) a clevis coupled to said distal end of said conduit, wherein said jaws are hingedly disposed on said clevis.

7. An endoscopic bipolar cauterizing biopsy forceps according to claim 6, wherein:

said clevis is non-conductive.

8. An endoscopic bipolar cauterizing biopsy forceps according to claim 7, wherein:

said clevis includes a clevis pin which is hingedly engaged by said jaws.

9. An endoscopic bipolar cauterizing biopsy forceps according to claim 8, wherein:

said clevis pin is non-conductive.

10. An endoscopic bipolar cauterizing biopsy forceps according to claim 8, further comprising:

f) non-conductive sleeve means for covering said clevis pin and for electrically insulating said clevis pin from said jaws.

11. An endoscopic bipolar cauterizing biopsy forceps according to claim 10, wherein:

said non-conductive sleeve means includes non-conductive washer means for electrically insulating said jaws from each other.

12. An endoscopic bipolar cauterizing biopsy forceps according to claim 2, wherein:

said actuation means includes a shaft with a longitudinal slot and a sliding member coaxial to said shaft with a member extending through said slot.

13. An endoscopic bipolar cauterizing biopsy forceps according to claim 12, wherein:

said electrical source coupling means comprises a conductive portion of said sliding member.

14. An endoscopic bipolar cauterizing biopsy forceps according to claim 13 wherein:

said sliding member comprises a pair of electrically conductive plates each with a pull wire hole, and said proximal end of each of said pull wires includes a Z-bend engaging a respective one of said pull wire holes.

15. An endoscopic bipolar cauterizing biopsy forceps according to claim 1, wherein:

said conduit comprises a flexible coil.

16. An endoscopic bipolar cauterizing biopsy forceps according to claim 7, further comprising:

f) a non-conductive unit having a solid clevis pin integral with a non-conductive washer means for electrically insulating said jaws from each other, said solid clevis pin having ends coupling with said clevis.

17. An endoscopic bipolar cauterizing biopsy forceps according to claim 16, wherein:

said solid clevis pin is stepped to form a seat on which said non-conductive clevis sits.

18. An endoscopic bipolar cauterizing biopsy forceps for use with an electrical cautery supply, comprising:

a) a tightly wound flexible coil having proximal and distal ends;

b) a clevis coupled to said distal end of said flexible coil, said clevis having a clevis pin;

c) a pair of opposed substantially hollow jaws hingedly disposed about said clevis pin, said jaws each having a proximal end portion with an electrically conductive portion and a distal end portion with an electrically conductive surface portion, wherein said electrically conductive portion of said proximal end portion and said electrically conductive surface portion of said distal end portion are electrically coupled to each other, and said electrically conductive portions of each of said opposed jaws are insulated from each other when said opposed jaws are in an open position, and said electrically conductive surface portion of each of said opposed jaws is a relatively substantially small portion of an outer surface of said distal end portion;

d) a pair of flexible electrically conductive pull wires, each having a proximal and a distal end, said pull wires extending through said coil and insulated from each other in said coil, the distal end of each of said pull wires being mechanically and electrically coupled to the electrically conductive proximal end portion of a respective one of said opposed jaws;

e) actuation means disposed at the proximal end of said flexible coil and coupled to said pull wires for moving said pull wires to open and close said jaws relative to each other; and f) electrical source coupling means electrically coupled to said proximal ends of said pull wires for coupling the electrical cautery supply to said pull wires.

19. An endoscopic bipolar cauterizing biopsy forceps according to claim 18, wherein:

said distal end portions of said jaws have cutting edges including a plurality of teeth extending therefrom, and said relatively substantially small conductive surface portion is located on at least one of said plurality of teeth.

20. An endoscopic bipolar cauterizing biopsy forceps according to claim 19, further comprising:

g) non-conductive sleeve means for covering said clevis pin and for electrically insulating said clevis pin from said jaws.

21. An endoscopic bipolar cauterizing biopsy forceps according to claim 20, wherein:

said non-conductive sleeve means includes non-conductive washer means for electrically insulating said jaws from each other.

22. An endoscopic bipolar cauterizing biopsy forceps according to claim 21, wherein:

said jaws are metal jaws which are coated with a thin layer of insulating polymer.

23. An endoscopic bipolar cauterizing biopsy forceps according to claim 18, wherein:

said clevis pin is a solid non-conductive clevis pin which is integral with a non-conductive washer means for electrically insulating said jaws from each other, said solid clevis pin having ends coupling with said clevis.

24. An endoscopic bipolar cauterizing biopsy forceps according to claim 23, wherein:

said solid clevis pin is stepped to form a seat on which said non-conductive clevis sits.

25. A bipolar cauterizing forceps for use with an electrical cautery supply having bipolar electrical connections, comprising:

a) a conduit having proximal and distal ends;

b) a pair of articulable opposed jaws located at said distal end of said conduit, each of said jaws having at least a portion that is electrically conductive, each of said jaws being electrically insulated from each other when said opposed jaws are in an open position, each of said jaws defining a cup for receiving a biopsy sample;

c) a pair of flexible electrically conductive pull wires, each having a proximal and a distal end, said pull wires extending through said conduit and insulated from each other in said conduit, the distal end of each of said pull wires being mechanically and electrically coupled to a respective one of said jaws at the portion of said jaw that is electrically conductive, and the proximal ends of said pull wires being capable of being coupled to the electrical cautery supply; and d) actuation means disposed at the proximal end of said conduit and coupled to said pull wires for moving said pull wires to open and close said jaws relative to each other.

26. A forceps according to claim 25, wherein:

said conduit is made of an electrically non-conducting material.

27. A forceps according to claim 25, wherein:

said pull wires are insulated from said conduit.

28. A forceps according to claim 25, wherein:

said opposed jaws each have a distal end, an electrically conductive inner core, and an electrically non-conductive outer surface covering all but a portion of the distal ends of the jaws directly opposite each other.

29. A forceps according to claim 28, wherein:

said non-conductive outer surface is a molded non-conductive body and said inner core is a conductive skeleton insert molded in said non-conductive body.

30. A forceps according to claim 25, wherein:

each of said opposed jaws has a distal portion, comprises an injection molded non-conductive body with electrically conductive plated teeth on the distal portion of said jaw, said teeth electrically coupled to said electrically conductive portion of said jaw.

* * * * *